United States Patent
Sun

(10) Patent No.: US 10,600,952 B2
(45) Date of Patent: Mar. 24, 2020

(54) SURFACE ACOUSTIC WAVE SENSOR COATING

(71) Applicant: Pulmostics Limited, Dublin (IE)

(72) Inventor: Yin Sun, Bridgewater, NJ (US)

(73) Assignee: Pulmostics Limited, Dublin (IE)

( * ) Notice: Subject to any disclaimer, the term of this patent is extended or adjusted under 35 U.S.C. 154(b) by 0 days.

(21) Appl. No.: 15/599,358

(22) Filed: May 18, 2017

(65) Prior Publication Data

US 2017/0338400 A1    Nov. 23, 2017

Related U.S. Application Data

(60) Provisional application No. 62/339,359, filed on May 20, 2016.

(51) Int. Cl.
*G01N 29/02* (2006.01)
*H01L 41/113* (2006.01)
(Continued)

(52) U.S. Cl.
CPC ........ *H01L 41/1132* (2013.01); *G01N 29/022* (2013.01); *G01N 29/036* (2013.01);
(Continued)

(58) Field of Classification Search
CPC .......... G01N 1/28; G01N 29/02; G01N 29/14; G01N 29/24; G01N 29/32; G01N 30/76;
(Continued)

(56) References Cited

U.S. PATENT DOCUMENTS 4,735,906 A * 4/1988 Bastiaans ............. G01N 29/022
  324/71.1
5,448,126 A * 9/1995 Eda ..................... H03H 9/02976
  310/313 A (Continued)

FOREIGN PATENT DOCUMENTS

WO    WO-0068419 A2 *  11/2000  ........... G01N 29/022
WO    2004079360 A1     9/2004

OTHER PUBLICATIONS

Xue, Zhongxin, Mingjie Liu, and Lei Jiang. "Recent developments in polymeric superoleophobic surfaces." Journal of Polymer Science Part B: Polymer Physics 50.17 (2012): 1209-1224.*

(Continued)

*Primary Examiner* — Daniel S Larkin
(74) *Attorney, Agent, or Firm* — Stetina Brunda Garred & Brucker

(57) ABSTRACT

A surface acoustic wave sensor in which instrument drift resulting from accumulated surface contamination is minimized. The sensor includes a piezoelectric substrate defined by an outer surface and a plurality of interdigitated electrodes mounted thereon. The electrodes are defined by one or more exposed portions and an unexposed portion abutting the outer surface of the piezoelectric substrate. An inert coating layer on the outer surface of the piezoelectric substrate and the exposed portions of the electrodes is provided, and can be a perfluoro-silane type compound, a perfluoro-trichloro-silane type compound, a perfluoro-acrylate type compound, polytetrafluoroethylene, or heptadecafluorodecyltrimethoxysilane.

21 Claims, 3 Drawing Sheets

(51) Int. Cl.
*G01N 1/28* (2006.01)
*G01N 29/14* (2006.01)
*G01N 29/24* (2006.01)
*G01N 29/32* (2006.01)
*G01N 30/76* (2006.01)
*H01L 41/047* (2006.01)
*H01L 41/053* (2006.01)
*H01L 41/18* (2006.01)
*G01N 29/036* (2006.01)

(52) U.S. Cl.
CPC ..... *G01N 29/2443* (2013.01); *G01N 29/2462* (2013.01); *G01N 29/32* (2013.01); *G01N 30/76* (2013.01); *H01L 41/0472* (2013.01); *H01L 41/0533* (2013.01); *H01L 41/18* (2013.01); *G01N 2291/021* (2013.01); *G01N 2291/0255* (2013.01)

(58) Field of Classification Search
CPC ... H01L 41/113; H01L 41/047; H01L 41/053; H01L 41/18
See application file for complete search history.

(56) References Cited

U.S. PATENT DOCUMENTS

| | | | | |
|---|---|---|---|---|
| 5,705,399 | A * | 1/1998 | Larue | G01N 33/5438 310/311 |
| 6,670,286 | B1 * | 12/2003 | Yang | G01N 29/022 427/100 |
| 7,052,468 | B2 * | 5/2006 | Melker | G01N 29/022 600/529 |
| 7,134,319 | B2 * | 11/2006 | Liu | G01N 29/022 73/31.06 |
| 7,383,731 | B2 * | 6/2008 | Liu | A47J 37/1266 73/54.01 |
| 2002/0009603 | A1 * | 1/2002 | McGill | B01J 20/285 428/447 |
| 2003/0053936 | A1 * | 3/2003 | Potyrailo | G01N 21/1702 422/82.11 |
| 2004/0242822 | A1 * | 12/2004 | Gawrisch | C08F 222/20 526/266 |
| 2006/0288774 | A1 | 12/2006 | Jacob et al. | |
| 2007/0160850 | A1 * | 7/2007 | Zhang | B27K 3/15 428/421 |
| 2008/0100176 | A1 * | 5/2008 | Haskell | G01H 11/08 310/313 R |
| 2008/0213853 | A1 * | 9/2008 | Garcia | B01F 13/0071 435/173.1 |
| 2009/0280031 | A1 * | 11/2009 | Serban | G01N 29/022 422/83 |
| 2010/0107285 | A1 * | 4/2010 | Ekinci | G01N 29/036 850/15 |
| 2010/0159195 | A1 * | 6/2010 | Quincy, III | B05D 5/083 428/141 |
| 2011/0053139 | A1 * | 3/2011 | Larson | G01N 33/54373 435/5 |
| 2012/0051018 | A1 * | 3/2012 | Ollgaard | B05D 1/62 361/781 |
| 2013/0244001 | A1 * | 9/2013 | Wang | C23C 8/42 428/141 |
| 2013/0280485 | A1 | 10/2013 | Coclite et al. | |
| 2013/0330247 | A1 | 12/2013 | Wilson et al. | |
| 2015/0020379 | A1 | 1/2015 | Engelkes et al. | |
| 2015/0111765 | A1 * | 4/2015 | Laury-Kleintop | G01N 29/022 506/9 |
| 2016/0313316 | A1 * | 10/2016 | Yao | G01N 29/22 |
| 2017/0191955 | A1 * | 7/2017 | Zou | C08L 39/06 |

OTHER PUBLICATIONS

Chu, Zonglin, and Stefan Seeger. "Superannphiphobic surfaces." Chemical Society Reviews 43.8 (2014): 2784-2798.*

Valipour, M. N., F. Ch Birjandi, and J. Sargolzaei. "Super-non-wettable surfaces: a review." Colloids Surf. A Physicochem. Eng. Asp 448 (2014): 93-106.*

McHale, G. S. N. J., N. J. Shirtcliffe, and M. I. Newton. "Super-hydrophobic and super-wetting surfaces: analytical potential?." Analyst 129.4 (2004): 284-287.*

Piech, Martin, Thomas L. Sounart, and Jun Liu. "Influence of surface morphology on the wettability of microstructured ZnO-based Surfaces." The Journal of Physical Chemistry C 112.51 (2008): 20398-20405.*

Zhang, Xi, et al. "Superhydrophobic surfaces: from structural control to functional application." Journal of Materials Chemistry 18.6 (2008): 621-633.*

PCT Search Report and Written Opinion for Application No. PCT/US2017/033556; dated Jul. 31, 2017.

* cited by examiner

SURFACE ACOUSTIC WAVE SENSOR COATING

CROSS-REFERENCE TO RELATED APPLICATION(S)

This application relates to and claims the benefit of U.S. Provisional Application No. 62/339,359 filed May 20, 2016 and entitled "SURFACE ACOUSTIC WAVE SENSOR COATING," the entire disclosure of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to surface acoustic wave (SAW) sensors employed in the identification of chemicals, and more particularly to coatings applied to SAW sensors to reduce surface contamination due to chemical adsorption.

2. Related Art

Surface acoustic wave (SAW) devices are widely used in chemical detection sensor applications. A SAW sensor is generally defined by an input transducer, which converts a known input electronic signal into an acoustic/mechanical wave, and an output transducer that converts that wave back into an electronic signal for further processing. The transducers, which are interdigitated, are disposed on a piezoelectric substrate such as quartz. There are generally two types of SAW sensor configurations based upon different electrode patterns. One of these configurations is referred to as a resonator, where a first set of reflector electrodes and a second set of reflector electrodes surrounds a set of interdigitated electrodes. The other configuration is referred to as a delay line, where the input interdigitated transducer electrodes are spaced apart from the output interdigitated transducer electrodes.

The frequency of the output electronic signal may vary due to mass loading on the SAW surface. When the surface is clean and free from additional mass loading, the output electronic signal has known characteristics, that is, known frequency. With additional mass loading, the oscillation frequency is reduced, and there is understood to be a linear relation between the additional mass and the reduction in oscillation frequency. This behavior may be utilized for detecting and identifying various chemical compounds.

A SAW detector may be comprised of multiple SAW sensors that are coated with selected polymers and define a sensor array. The particular polymer used for the coating is understood to enhance the adsorption of certain chemical compounds, or groups of chemical compounds, and selectivity of the polymers is understood to be based upon the function groups thereof. The adsorption is understood to increase the mass loading on the sensor surface, resulting in the reduction of the oscillation frequency. Each sensor in the array is understood to respond different to specific target chemical compounds, target groups of chemical compounds, and target mixtures of different chemical compounds. Response patterns for each of the foregoing may be established. The coating polymers are thus selected based upon the targets to be detected, and the selective adsorption capabilities of the coating surface are enhanced therefor. Thus, selectivity and sensitivity of the sensors may be optimized to detect the target chemical compounds.

With such types of sensors, the chemical compound samples interact directly with the polymer rather than the SAW surface. The adsorption of the chemical molecules by the polymer coating increases the mass loading on the SAW surface, which in turn reduces the oscillation frequency of the SAW as discussed above. There is understood to be no interaction between the chemical compound sample and the SAW device surface.

Alternatively, uncoated SAW devices may be used as sensors, specifically for gas chromatography applications and detectors therefor. Initially, the chemical compounds are separated in a gas chromatography column. When the vapor of a chemical compound elutes from the gas chromatography column, such vapor contact the uncoated SAW sensor. The chemical compound is understood to condense onto the surface of the sensor when the SAW temperature thereof is below the dew point of the vapor. The condensed chemical compound, in turn, affects the oscillation frequency of the SAW device. Detection and identification of the chemical compound sample is based upon the alteration to the oscillation frequency, and the retention time in the gas chromatography column.

With these sensors, chemical compounds are understood to interact directly with the surface of the SAW device without any barrier against the condensate, with the mass loading of the chemical by condensation being the basis for the sensor response. When the concentration in the eluting vapor is below the saturation level at the sample vapor-SAW interface, each chemical compound evaporates from the SAW surface without an increase in the temperature of the SAW sensor.

There are generally three contributors to the mass loading on the surface of uncoated SAW devices. First, there is condensation due to the saturation of chemical compounds in the vapor in contact with the SAW sensor. Chemical compounds loaded on the surface via condensation evaporate when the concentration in the contacted vapor is below the saturation level at the sample vapor-SAW surface interface. It is not necessary for the SAW sensor to be heated to release the condensed chemical compounds, and the release is understood to be complete without any residues remaining on the surface of the SAW sensor. If the chemical compounds load on the SAW sensor surface only by this process, short and long term operational stability is possible.

Second, there is physical adsorption due to weak Van der Waals forces between the substrate surface and the molecules in the vapor. Such adsorption may require external energy to reverse, and completely release the adsorbed chemical compounds. As the bond is based upon weak Van der Waals forces, only a slight increase in temperature of the SAW sensor may be needed to break the bond. It is understood that residues do not remain on the surface, and therefore raising the temperature of the sensor by a proscribed degree after each analysis cycle is deemed sufficient to clean the chemical compounds physically adsorbed on the SAW sensor surface.

Third, there is chemical adsorption due to the formation of chemical bonds between the active sites of the substrate/quartz surface and the interdigitate electrodes, and the molecules in the vapor. For example, although the surface of the quartz substrate, which is one of the most used piezoelectric materials for a SAW device, is generally regarded as inert, they are slightly acidic and highly adsorptive due to the presence of hydroxyl groups (—OH). Such reactive groups are understood to interact with different function groups such as amine (—NH), carboxylic acid (—COOH), hydroxyl (—OH), or thiol (—SH) via hydrogen bonding. The reaction between the SAW surface and the function groups results in the chemical adsorption of the compounds that contain such function groups into untreated surfaces of the SAW sensor. Chemical compounds in a sample being analyzed which contain these function groups are understood to bond to the surface of the SAW sensor, and cannot be removed without significant external energy. Furthermore, the chemical compounds that remain on the surface of the SAW sensor may create different active sites thereon and react with other chemical compounds, thereby increasing its chemical adsorption capability for those chemical compounds in contact with the surface of the SAW sensor. Over time and multiple analysis cycles, there may be an accumulation of residual compounds that, in turn, affect the oscillation frequency, resulting in instrument drift. When residual chemical compounds have accumulated beyond a certain point, oscillation may be reduced to such an extent that there will be no further response to additional mass. This is understood to affect both long term stability and repeatability.

To minimize accumulation of residual compounds on the SAW sensor, presently, the sensor is briefly heated to a higher temperature at the end of each analysis cycle than during analysis. This is understood to break the chemical bond between the surface of the SAW sensor and the chemically adsorbed chemical compounds, and release the adsorbed molecules following each analysis cycle. Under some circumstances, it may not be possible to completely reverse the chemical adsorption, even with high temperatures. The aforementioned chemical reactions between the SAW sensor and the compounds, and the attendant chemical bonds formed as a consequence, may prevent full removal. Thus, the surface of the SAW sensor may not be entirely clean, or as clean as its initial state, if a high amount of chemical compounds have been chemically adsorbed. Heavily contaminated sensors require heating for longer durations and at higher temperatures. Where heating the SAW sensor is insufficient, conventionally they may be washed with solvents such as acetone. To the extent a solvent wash is also insufficient, the SAW sensor may require replacement.

Accordingly, there is a need in the art for an improved, uncoated SAW sensor that is not susceptible to chemical adsorption of the analyzed chemical compound sample. There is also a need in the art for such SAW sensors with both short term and long term stability.

BRIEF SUMMARY

The present disclosure contemplates a surface acoustic wave sensor that overcomes instrument drift resulting from accumulated surface contamination. More particularly, various embodiments are directed to a surface acoustic wave sensor with a piezoelectric substrate defined by an outer surface, and a plurality of interdigitated electrodes mounted on the outer surface of the piezoelectric substrate. The electrodes may be defined by one or more exposed portions and an unexposed portion abutting the outer surface of the piezoelectric substrate. The surface acoustic wave sensor may also include an inert coating layer on the outer surface of the piezoelectric substrate and the exposed portions of the electrodes. The inert coating layer may be selected from a group consisting of a perfluoro-silane type compound, a perfluoro-trichloro-silane type compound, a perfluoro-acrylate type compound, polytetrafluoroethylene, and heptadecafluorodecyltrimethoxysilane. An example of the coating materials is 1H, 1H, 2H, 2H-perfluorooctyltriethoxysilane. The inert coating may react with the piezoelectric substrate, such as quartz, and a low energy surface may be defined thereby.

The present disclosure will be best understood accompanying by reference to the following detailed description when read in conjunction with the drawings.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The present disclosure is directed to various embodiments of a surface acoustic wave (SAW) sensor device utilized in chemical analysis systems. In accordance with these embodiments, these improved sensor devices overcome instrument drift that occurs as a consequence of surface contamination over repeated analysis cycles. As will be described in further detail below, these embodiments may utilize a thin or monolayer of an inert polymer material that coats an entirety of the exposed sensor device. The detailed description set forth below in connection with the appended drawings is intended as a description of the several presently contemplated embodiments of these sensor devices, and is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second, outer and inner, distal and proximal, and the like are used solely to distinguish one from another entity without necessarily requiring or implying any actual such relationship or order between such entities.

Figure 1A:
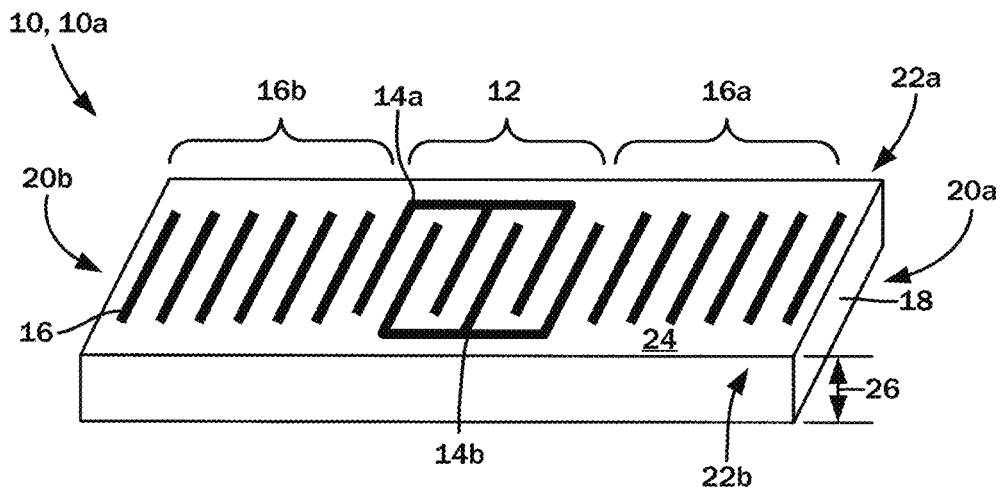
FIG. 1A is a perspective view of one implementation of a resonator surface acoustic wave (SAW) sensor device that may be utilized in one or more embodiments of the present disclosure.
Figure 1B:
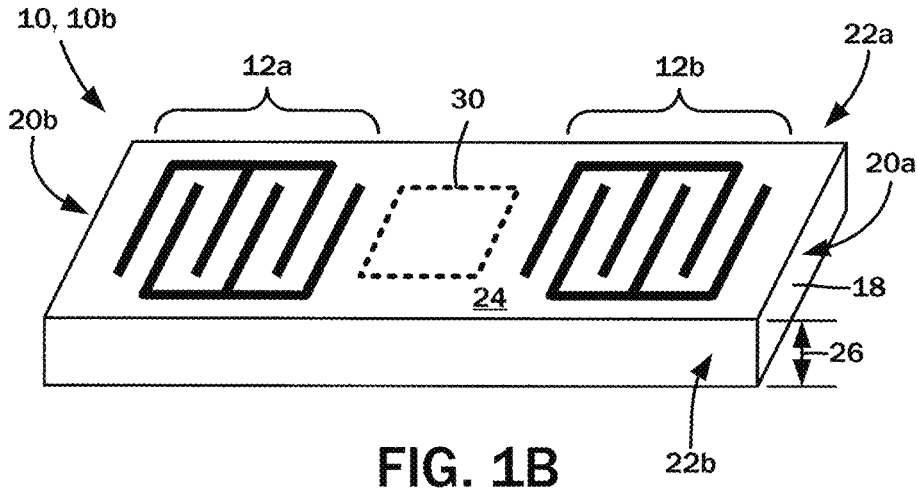
FIG. 1B is a perspective view of an implementation of a delay line SAW sensor device that may be utilized in one or more embodiments of the present disclosure.

FIGS. 1A and 1B illustrate two variations of a SAW sensor device 10 that may be utilized in a chemical analysis system. FIG. 1A shows a resonator type SAW sensor device 10a, while FIG. 1B shows a delay line type SAW sensor device 10b. In accordance with the present disclosure, other types of SAW sensor devices known in the art may be readily substituted without departing from the scope of the present disclosure. Broadly, a sensor based upon a SAW device compares an input signal to an output signal differing in frequency after the signal is transduced to a surface acoustic wave that passes through a substrate. The frequency of the surface acoustic wave are understood to change based upon the mass loading from a sample chemical compound introduced on to the sensor surface.

The input signal is provided to a transducer, also referred to as interdigitated electrodes (IDEs) 12. In the resonator type SAW sensor device 10a shown in FIG. 1A, the IDE 12 may include a first port 14a corresponding to an input, and a second port 14b may correspond to an output. The IDEs 12 may be surrounded on both sides by respective sets of reflector electrodes 16a and 16b. The IDEs 12 and the reflector electrodes 16a, 16b are understood to be mounted on to a piezoelectric substrate 18. In further detail, the piezoelectric substrate 18 has a generally quadrangular configuration defined by a right side 20a and an opposed left side 20b, as well as an upper end 22a and an opposed lower end 22b. The piezoelectric substrate 18 is also defined by a prescribed thickness 26 with a top surface 24. The IDEs 12 are mounted on the top surface 24 in a central region of the piezoelectric substrate 18, with the reflector electrodes 16a being disposed toward the right side 20a and the reflector electrodes 16b being disposed toward the left side 20b.

The piezoelectric substrate 18 is typically fabricated from a quartz material. The material for the electrodes, whether it be the reflector electrodes 16a, 16b, or the IDEs 12, may be gold or aluminum. It will be appreciated by those having ordinary skill in the art that the aforementioned selection of materials is presented by way of example only and not of limitation.

The IDEs 12 are understood to transduce the input electrical signal to surface acoustic waves. The reflector electrodes 16a, 16b are understood to generate a resonance as the surface acoustic waves are reflected. The chemical compound sample is introduced to the surface of the SAW sensor device 10, thereby affecting the propagation/resonance of the surface acoustic wave thereon. The resonant surface acoustic waves are converted back to electrical signals, and compared against the input electrical signal.

FIG. 1B, as noted above, is a delay line type SAW sensor device. There is a first set of IDEs 12a that are designated for the input, and a second set of IDEs 12b that are designated for the output. Again, the IDEs 12 are mounted onto the top surface 24 of the piezoelectric substrate 18, with the first set of IDEs 12a being spaced apart from the second set of IDEs 12b. Specifically, the first set of IDEs 12a are mounted toward the right end 20a of the piezoelectric substrate 18, while the second set of IDEs 12b are mounted toward the left end 20b. The area between the first and second set of IDEs 12 may be referred to as a delay line 30. A chemical compound sample may be introduced on to the SAW sensor device 10, which alters the surface acoustic wave being propagated across the delay line 30. The resultant change in characteristics, e.g, the frequency, amplitude, phase, and time delay that is present on the transduced output electrical signal is understood to correspond to a specific mass loading.

Figure 2:
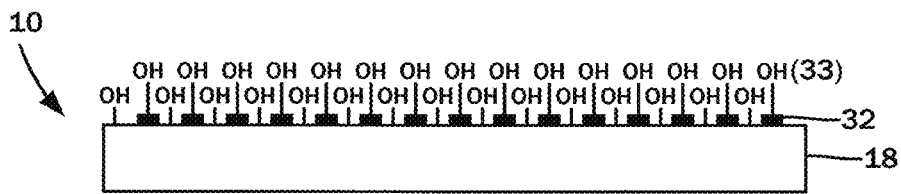
FIG. 2 is a cross-sectional view of an exemplary SAW sensor device, with hydroxyl group sites on the surface being depicted.

FIG. 2 is a cross sectional view of the SAW sensor device 10a, with its plurality of electrodes 32 corresponding to the IDEs 12 and reflector electrodes 16 mounted onto the piezoelectric substrate 18. Additionally depicted is the hydroxyl group sites 33 that are on the exposed surfaces. As indicated above, otherwise exposed quartz surfaces are slightly acidic and highly adsorptive because of these hydroxyl groups. These reactive groups are understood to interact via hydrogen bonding with chemical compounds having different function groups such as amine (—NH), carboxylic acid (—COOH), hydroxyl (—OH) and thiol (—SH).

Figure 3:
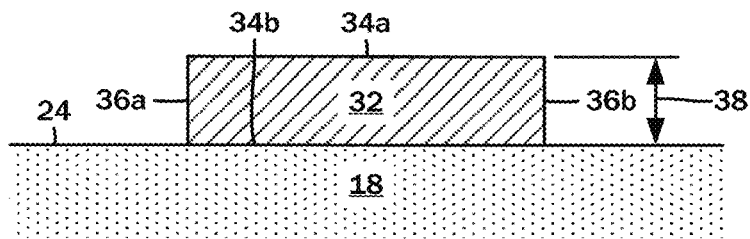
FIG. 3 is a detailed cross-sectional view of an electrode mounted to the substrate of the SAW sensor device.

With further reference to FIG. 3, the electrode 32 is defined by a top surface 34a and an opposed bottom surface 34b that abuts against the top surface 24 of the piezoelectric substrate 18. The electrode 32 is further defined by a first side segment 36a and an opposed second side segment 36b, both of which are orthogonal to the top surface 34a and the bottom surface 34b. In this regard, a thickness 38 is defined by the electrode 32. The top surface 34a and the side segments 36a, 36b of the electrode 32 are exposed, as is the top surface 26 of the piezoelectric substrate 18. Although the figures illustrate a perpendicular relationship between the top surface 34a and the side segments 36, this is by way of example only and not of limitation. When manufactured, the electrode 32 and the piezoelectric substrate 18 may exhibit less than perfect perpendicular corners as otherwise depicted herein.

According to one contemplated embodiment of the present disclosure, the SAW sensor device 10 includes an inert coating layer 40 that is applied to the exposed portions of the electrodes 32 and the piezoelectric substrate 18, that is, the top surface 34a and the side segments 36a, 36b of the electrode 32, as well as the top surface 26 of the piezoelectric substrate 18. The inert coating layer 40 is understood to be a polymer material, and may be applied to the piezoelectric substrate 18 and the electrodes 32 by techniques that do not involve direct surface to liquid contact such as chemical vapor deposition (CVD), as well as those techniques that do involve direct surface to liquid contact such as dip coating and spin coating. It is expressly contemplated that the SAW sensor device 10 be coated prior to assembly of a chemical analysis system, though the existing chemical analysis systems may be retrofitted with newly coated SAW sensor devices 10.

Figure 4A:
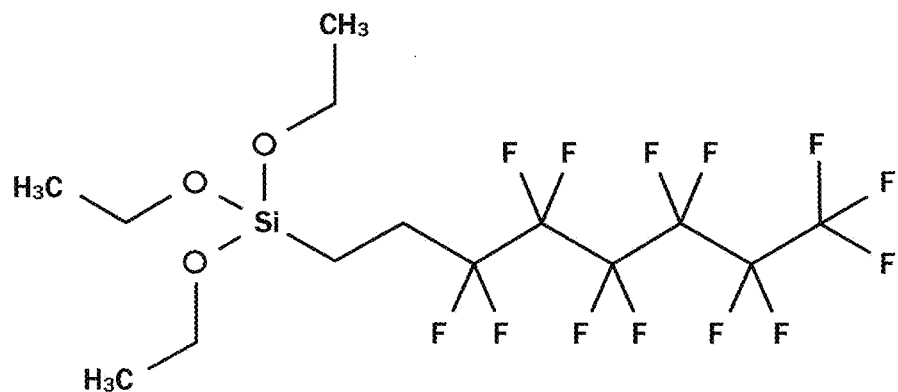
FIGS. 4A-4D illustrate the molecular structures of the possible coating materials that may be utilized in accordance with various embodiments of the present disclosure.

A variety of different materials are contemplated to the inert coating layer 40. In one embodiment, the material may be a perfluoro-silane type chemical compound. One example of this type of polymer is 1H, 1H, 2H, 2H-perfluorooctyltriethoxysilane, which may be commercially available as referenced by Chemical Abstracts Service (CAS) no. 51851-37-7. This is the preferred, though optional polymer for the inert coating layer 40. The molecular structure of this material is shown in FIG. 4A. Another example of this type of polymer is 1H, 1H, 2H, 2H-perfluorodecyltriethoxysilane, which may be commercially available as referenced by CAS no. 101947-16-4.

Figure 4B:
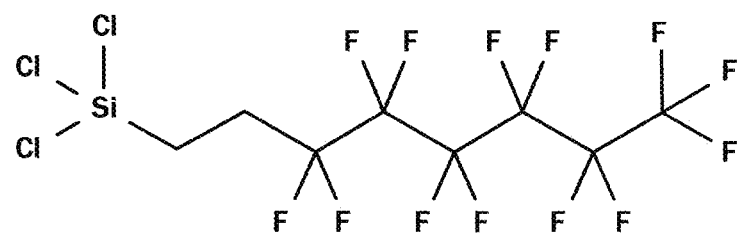

Another embodiment contemplates the material being a perfluoro-trichloro-silane type chemical compound. An example of this type of polymer is 1H, 1H, 2H, 2H-perfluorooctyltrichlorosilane, which may be commercially available as referenced by CAS no. 78560-45-9. The molecular structure of this material is shown in FIG. 4B. Yet another example of this type of polymer is 1H, 1H, 2H, 2H-perfluorododecyltrichlorosilane, which may be commercially available as referenced by CAS no. 102488-49-3.

Figure 4C:
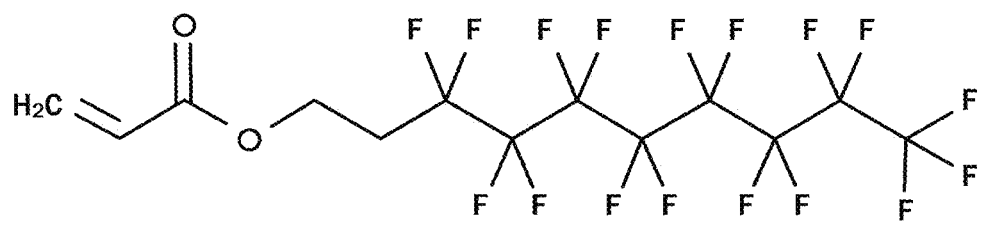

Other embodiments contemplate the coating material being a perfluoro-acrylate type chemical compound. One example of this type of polymer is 1H, 1H, 2H, 2H-prefluorodecylacrylate, which may be commercially available as referenced by CAS no. 27905-45-9. The molecular structure of this material is shown in FIG. 4C.

Figure 4D:
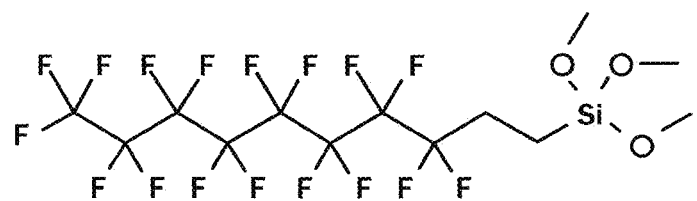

Further, the present disclosure contemplates the use of polytetrafluoroethylene (PTFE), which may be commercially available as referenced by CAS no. 9002-84-0, as well as 1,1,1,3,3,3-hexamethyldisilazane, which may be commercially available as referenced by CAS no. 999-97-3. Yet another coating material that may be utilized is (heptadecafluoro-1,1,2,2-tetrahydro-decyl)-1-trimethoxysilane, which may be commercially available as referenced by CAS no. 83048-65-1. The molecular structure of this material is shown in FIG. 4D.

Figure 5:
FIG. 5 is a cross-sectional view of the SAW sensor device showing the active regions prior to coating with an inert material.
Figure 6:
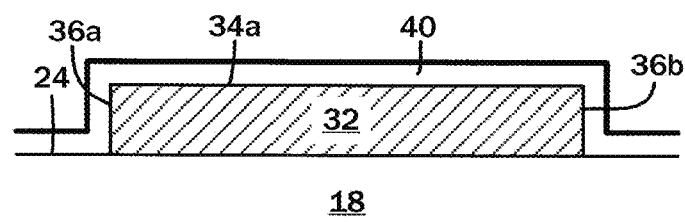
FIG. 6 is a detailed cross-sectional view of the SAW sensor device with the electrode and the substrate coated with the inert material in accordance with various embodiments of the present disclosure.

Referring now to the cross-sectional view of the SAW sensor device 10 shown in FIG. 5, when uncoated, there are multiple active sites 33 on the SAW surface, including the piezoelectric substrate 18 and electrodes 32. Regardless of the specific one selected, the coating material is understood to react with the active sites 33 to form a chemical bond. That is, the hydroxyl active sites on the surface bond with the molecules of the coating material, and are therefore unavailable to react with any other chemicals, including those that are part of sample under analysis. As shown in the detailed view of FIG. 6, the inert coating material forms a very thin layer or a monolayer on the top surface 24 of the piezoelectric substrate 18, the top surface 34a of the electrode 32, as well as the side segments 36a, 36b of the same. As referenced herein, a thin layer of the coating material is contemplated to be a thickness of less than 5 microns.

Figure 7:
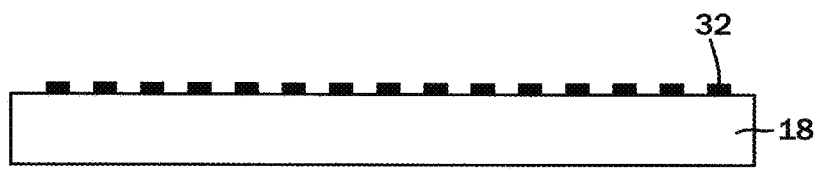
FIG. 7 is a cross-sectional view of the SAW sensor device after being coated with the inert material, illustrating the lack of active regions.

As a result of the inert property of the coating material, the surface energy is understood to be low, and the active sites on the surface of the SAW sensor device 10 is greatly reduced, if not eliminated, as shown in FIG. 7. The surface of the SAW sensor device 10 is understood to be covered with long —CF2, —CF3, or —CH3 chains, which have very low surface energy and therefore does not react with other chemicals under normal operating conditions of the chemical analysis system.

With the inert coating layer, it is expressly contemplated that mass loading of the SAW sensor device 10 via condensation and physical adsorption. The surface may therefore be readily cleaned without heating to the SAW sensor device 10 to much higher temperatures. The condensation/adsorption process occurring over an analysis cycle is thus understood to be reversible. As such, it is possible for the SAW sensor device 10 to be used over extended service cycles without the accumulation of residue from chemical adsorption without a long-term degradation in stability and repeatability. As a typical SAW sensor device 10 is hosted within an analysis chamber, it is generally isolated from mechanical wear and exposure to direct sunlight. Furthermore, the selected material for the inert coating layer 40 is understood to be thermally stable with a high point of 192° without decomposition. It will be appreciated by those having ordinary skill in the art that these materials are also robust and chemically stable over long durations.

The addition of the inert coating layer 40 is understood to decrease the frequency of the surface acoustic wave being propagated on the SAW sensor device 10. However, it is understood, based on preliminary testing, that sensitivity is affected only slightly because of the thinness of the inert coating layer 40. This is expected as a consequence of the monolayer, and the minimal mass of the coating material on the surface of the SAW sensor device 10. In a test analysis of alkanes under the same conditions and concentration level, the uncoated SAW sensor device 10 has been measured to be slightly higher in responses than with the coated variation.

As indicated above, the inert coating layer 40 may be applied to the SAW sensor device 10 before assembly of the chemical analysis system, or on a SAW sensor device 10 being used in an existing installation. Furthermore, a variety of methods for disposing the coating materials on the SAW sensor device 10 are contemplated, including chemical vapor deposition, dipping, and so forth.

With a chemical vapor deposition (CVD) method, by way of example, a small volume of the coating material, e.g., less than 1 mL, may be transferred to a container. As noted earlier, the preferred, though optional material is 1H, 1H, 2H, 2H-perfluorooctyltriethoxysilane. A small volume of deionized water, e.g., less than 1 mL, may similarly be placed in a separate container. The base uncoated SAW sensor device 10, which may be provided in single die form or as a set of multiple dies in a wafer, is thoroughly cleaned with organic solvents and deionized water. The SAW sensor device 10, together with the coating material in the first container and the deionized water in the second container, is then placed into a temperature-controlled vacuum chamber side-by-side. The vacuum chamber is then closed, and is evacuated to a prescribed pressure. Upon reaching the prescribed pressure, the inlet/outlet of the vacuum chamber may be closed off. Preferably, the pressure is the minimum possible with the particular vacuum chamber. The interior of the vacuum chamber is then heated to 120° C. for four (4) hours, and the deionized water and the coating material is removed therefrom. The SAW sensor device 10 is kept in the vacuum chamber, and is heated to 140° C. for two (2) hours. Following this second heating process, the SAW sensor device 10 is removed from the vacuum chamber and washed with organic solvents and deionized water to remove excess coating material. After air-drying, the SAW sensor device 10 is ready for use.

With a dip coating method, by way of example, the coating material may be prepared as a solution. In one exemplary implementation, the coating material is 1H, 1H, 2H, 2H-perfluorooctyltriethoxysilane, and is prepared as a methanol solution of hydrolyzed material by 1% weight. The SAW sensor device 10 is placed in the solution for a short period of time, e.g., one (1) hour at room temperature. This is understood to allow the reaction between the surface of the SAW sensor device 10 and the coating material to occur. The SAW sensor device 10 is then removed from the solution, and rinsed with ethanol. Non-bonded coating molecules may then be removed by heating the SAW sensor device 10 to 140° C. for one hour.

The foregoing coating methods and the particulars thereof are provided by way of example only and not of limitation. Any other suitable fabrication method may be readily substituted without departing from the scope of the present disclosure.

The above description is given by way of example, and not limitation. Given the above disclosure, one skilled in the art could devise variations that are within the scope and spirit of the features disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A surface acoustic wave sensor, comprising:
a piezoelectric substrate defined by an outer surface;
a plurality of interdigitated electrodes mounted on the outer surface of the piezoelectric substrate, the electrodes being defined by one or more outer portions and an inner portion abutting the outer surface of the piezoelectric substrate; and
a coating layer on the outer surface of the piezoelectric substrate and the outer portions of the electrodes, the coating layer selected from a group consisting of a perfluoro-silane type compound, a perfluoro-trichloro-silane type compound, a perfluoro-acrylate type compound, polytetrafluoroethylene, and heptadecafluorodecyltrimethoxysilane.

2. The surface acoustic wave sensor of claim 1, wherein the outer surface of the piezoelectric substrate defines one or more chemically active sites.

3. The surface acoustic wave sensor of claim 2, wherein the coating layer forms a chemical bond with the one or more chemically active sites on the outer surface of the piezoelectric substrate.

4. The surface acoustic wave sensor of claim 1, wherein the coating layer is a monolayer.

5. The surface acoustic wave sensor of claim 1, wherein the coating layer is a thin layer of five (5) microns or less.

6. The surface acoustic wave sensor of claim 1, wherein the perfluoro-silane type compound is 1H, 1H, 2H, 2H-perfluorooctyltriethoxysilane.

7. The surface acoustic wave sensor of claim 1 wherein the perfluoro-silane type compound is 1H 1H, 2H, 2H-perfluorodecyltriethoxysilane.

8. The surface acoustic wave sensor of claim 1, wherein the perfluoro-trichloro-silane type compound is 1H, 1H, 2H, 2H-perfluorooctyltrichlorosilane.

9. The surface acoustic wave sensor of claim 1, wherein the perfluoro-trichloro-silane type compound is 1H, 1H, 2H, 2H-perfluorodecyltrichlorosilane.

10. The surface acoustic wave sensor of claim 1, wherein the perfluoro-acrylate type compound is 1H, 1H, 2H, 2H-perfluorodecyl acrylate.

11. The surface acoustic wave sensor of claim 1, wherein the coating layer is applied to the outer surface of the piezoelectric substrate and the outer portions of the electrodes by a chemical vapor deposition process.

12. The surface acoustic wave sensor of claim 1, wherein the coating layer is applied to the outer surface of the piezoelectric substrate and the outer portions of the electrodes by a dip coating process.

13. The surface acoustic wave sensor of claim 1, wherein the coating layer is applied to the outer surface of the piezoelectric substrate and the outer portions of the electrodes by a spin coating process.

14. The surface acoustic wave sensor of claim 1, wherein the coating layer coats an entirety of the outer surface of the piezoelectric substrate and an entirety of the outer portions of the electrodes.

15. A surface acoustic wave sensor, comprising:
a piezoelectric quartz substrate;
a plurality of interdigitated electrodes mounted to the piezoelectric substrate; and
a coating layer of 1H, 1H, 2H, 2H-perfluorooctyltriethoxysilane on the piezoelectric substrate and the electrodes;
wherein the coating layer forms a chemical bond with one or more chemically active sites on the piezoelectric substrate.

16. The surface acoustic wave sensor of claim 15, wherein the coating layer is a monolayer.

17. The surface acoustic wave sensor of claim 15, wherein the coating layer is a thin layer of five (5) microns or less.

18. The surface acoustic wave sensor of claim 15, wherein the coating layer is applied to the piezoelectric substrate and the electrodes by a chemical vapor deposition process.

19. The surface acoustic wave sensor of claim 15, wherein the coating layer is applied to the piezoelectric substrate and the electrodes by a dip coating process.

20. The surface acoustic wave sensor of claim 15, wherein the coating layer is applied to the piezoelectric substrate and the electrodes by a spin coating process.

21. A surface acoustic wave sensor, comprising:
a piezoelectric substrate;
a plurality of interdigitated electrodes mounted to the piezoelectric substrate; and
a coating layer on the piezoelectric substrate and the electrodes, the coating layer selected from a group consisting of a perfluoro-silane type compound, a perfluoro-trichloro-silane type compound, a perfluoro-acrylate type compound, polytetrafluoroethylene, and heptadecafluorodecyltrimethoxysilane;
wherein the coating layer forms a chemical bond with one or more chemically active sites on the piezoelectric substrate.

* * * * *